(12) United States Patent
Elomari et al.

(10) Patent No.: US 7,666,811 B2
(45) Date of Patent: *Feb. 23, 2010

(54) IONIC LIQUID CATALYST HAVING ENHANCED ACTIVITY

(75) Inventors: Saleh Elomari, Fairfield, CA (US); Thomas V. Harris, Benicia, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 488 days.

This patent is subject to a terminal disclaimer.

(21) Appl. No.: 11/315,750

(22) Filed: Dec. 20, 2005

(65) Prior Publication Data

US 2007/0142676 A1    Jun. 21, 2007

(51) Int. Cl.
*B01J 31/00* (2006.01)
*B01J 27/135* (2006.01)

(52) U.S. Cl. .................... 502/150; 502/152; 502/156; 502/158; 502/169; 502/172; 502/227

(58) Field of Classification Search ................ 502/150, 502/152, 156, 158, 169, 172, 227
See application file for complete search history.

(56) References Cited

U.S. PATENT DOCUMENTS

| | | | |
|---|---|---|---|
| 4,122,245 | A | 10/1978 | Nardi et al. |
| 4,463,071 | A | 7/1984 | Gifford et al. |
| 4,463,072 | A | 7/1984 | Gifford et al. |
| 5,104,840 | A | 4/1992 | Chauvin et al. |
| 5,731,101 | A | 3/1998 | Sherif et al. |
| 6,096,680 | A | 8/2000 | Park |
| 6,797,853 | B2 | 9/2004 | Houzvicka et al. |
| 2004/0077914 | A1 | 4/2004 | Zavilla et al. |
| 2004/0133056 | A1 | 7/2004 | Liu et al. |
| 2007/0004936 | A1* | 1/2007 | Ishihara et al. ............. 560/231 |

OTHER PUBLICATIONS

Adams et al.; Chem. Commun., 1998, 2097-2098.*
Chauvin, Yves et al.,Alkylation of isobutane with 2-butene using 1-butyl-3-methylimidazolium chloride-aluminium chloride molten salts as catalysts, Journal of Molecular Catalysis, 1994, 155-165, vol./Issue 92, Elsevier Science B V.
Zhao, Zhongkui et al., Effects of kinds of ionic liquid catalusts on alkylations of 1-and 2-methylnapthalene with alkenes, Applied Catalysis A: General, 2005, 133-137, vol./Issue 290, Elsevier Science B V.
Christopher J. Adams, et al., Stereoslective hydogenation reacations in chloroaluminate (III) ionic liquids: a new method for the reduction of aromatic compounds, Institute of Applied Catalysis, Schoold of Chemistry, 1999, 1043-1044, Received in Cambridge, UK) Feb. 15, 1999, Accepted Apr. 19, 1999.

* cited by examiner

*Primary Examiner*—Jerry Lorengo
*Assistant Examiner*—James E McDonough
(74) *Attorney, Agent, or Firm*—Susan M. Abernathy; Steven H. Roth

(57) ABSTRACT

A process for producing acidic ionic liquid catalyst having enhanced activity comprising combining fresh acidic ionic liquid catalyst, a metal and a Broensted acid in a reaction zone for a time sufficient to increase the activity of the ionic liquid catalyst is disclosed.

A process for producing acidic ionic liquid catalyst having enhanced activity comprising the steps of combining fresh ionic liquid catalyst, a metal and HCl in a reaction zone for a time sufficient to increase the activity of the fresh ionic liquid catalyst; removing reaction product from the reaction zone and recovering at least a portion of the treated ionic liquid catalyst is also disclosed.

9 Claims, No Drawings

IONIC LIQUID CATALYST HAVING ENHANCED ACTIVITY

FIELD OF THE INVENTION

The present invention relates to acidic ionic liquid catalysts and more specifically to the acidic ionic liquid catalysts having enhanced activity and methods for preparing them.

BACKGROUND OF THE INVENTION

Ionic liquids are liquids that are composed entirely of ions. The so-called "low temperature" Ionic liquids are generally organic salts with melting points under 100 degrees C., often even lower than room temperature. Ionic liquids may be suitable for example for use as a catalyst and as a solvent in alkylation and polymerization reactions as well as in dimerization, oligomerization acetylation, metatheses, and copolymerization reactions.

One class of ionic liquids is fused salt compositions, which are molten at low temperature and are useful as catalysts, solvents and electrolytes. Such compositions are mixtures of components which are liquid at temperatures below the individual melting points of the components.

Ionic liquids can be defined as liquids whose make-up is entirely comprised of ions as a combination of cations and anions. The most common ionic liquids are those prepared from organic-based cations and inorganic or organic anions. The most common organic cations are ammonium cations, but phosphonium and sulphonium cations are also frequently used. Ionic liquids of pyridinium and imidazolium are perhaps the most commonly used cations. Anions include, but not limited to, $BF_4^-$, $PF_6^-$, haloaluminates such as $Al_2Cl_7^-$ and $Al_2Br_7^-$, $[(CF_3SO_2)_2N]^-$, alkyl sulphates ($RSO_3^-$), carboxylates ($RCO_2^-$) and many other. The most catalytically interesting ionic liquids are those derived from ammonium halides and Lewis acids (such as $AlCl_3$, $TiCl_4$, $SnCl_4$, $FeCl_3$ ... etc). Chloroaluminate ionic liquids are perhaps the most commonly used ionic liquid catalyst systems.

Examples of such low temperature ionic liquids or molten fused salts are the chloroaluminate salts. Alkyl imidazolium or pyridinium salts, for example, can be mixed with aluminum trichloride ($AlCl_3$) to form the fused chloroaluminate salts. The use of the fused salts of 1-alkylpyridinium chloride and aluminum trichloride as electrolytes is discussed in U.S. Pat. No. 4,122,245. Other patents which discuss the use of fused salts from aluminum trichloride and alkylimidazolium halides as electrolytes are U.S. Pat. Nos. 4,463,071 and 4,463,072.

U.S. Pat. No. 5,104,840 describes ionic liquids which comprise at least one alkylaluminum dihalide and at least one quaternary ammonium halide and/or at least one quaternary ammonium phosphonium halide; and their uses as solvents in catalytic reactions.

U.S. Pat. No. 6,096,680 describes liquid clathrate compositions useful as reusable aluminum catalysts in Friedel-Crafts reactions. In one embodiment, the liquid clathrate composition is formed from constituents comprising (i) at least one aluminum trihalide, (ii) at least one salt selected from alkali metal halide, alkaline earth metal halide, alkali metal pseudohalide, quaternary ammonium salt, quaternary phosphonium salt, or ternary sulfonium salt, or a mixture of any two or more of the foregoing, and (iii) at least one aromatic hydrocarbon compound.

Aluminum-containing catalysts are among the most common Lewis acid catalysts employed in Friedel-Craft reactions. Friedel-Craft reactions are reactions which fall within the broader category of electrophylic substitution reactions including alkylations.

Other examples of ionic liquids and their methods of preparation may also be found in U.S. Pat. Nos. 5,731,101; 6,797,853 and in U.S. Patent Application Publications 2004/0077914 and 2004/0133056.

Catalysts are employed in various commercial and industrial applications to increase chemical reaction rates. Generally, it is desirable to be able to enhance catalyst activity since catalytic materials are typically expensive. Similarly, the equipment for catalyst handling can add to the cost. Any improvement in catalyst activity decreases these costs. Having a more active catalyst will allow the catalyst to be used longer before it becomes deactivated and requires replacement or regeneration. Higher catalyst activity will also allow the use of lower reaction temperatures or to operate with increased yield of products.

SUMMARY OF THE INVENTION

The present invention provides, among other things, a process for producing acidic ionic liquid catalyst having enhanced activity comprising combining freshly-made acidic ionic liquid catalyst, a metal and a Broensted acid in a reaction zone for a time sufficient to increase the activity of the ionic liquid catalyst.

In one embodiment, the present invention provides a process for producing acidic ionic liquid catalyst having enhanced activity comprising the steps of combining fresh ionic liquid catalyst, a metal and HCl in a reaction zone for a time sufficient to increase the activity of the fresh ionic liquid catalyst and recovering at least a portion of the treated ionic liquid catalyst. The activation treatment may be done in the presence of neutral hydrocarbons, i.e. normal paraffins, to aid in the stirring. In that case, the treated catalyst will be recovered by removing the hydrocarbon layer by decanting or other separation means of separation followed by filtering the catalyst from the metal and the produced metal halide.

DETAILED DESCRIPTION

The present invention relates to acidic ionic liquid-based catalysts having enhanced catalytic activity, which means that the catalyst demonstrates greater activity for catalyzing a chemical reaction than the corresponding freshly-made or untreated catalyst. The present process is being described and exemplified with reference certain specific ionic liquid catalysts and processes catalyzed thereby, but such description is not intended to limit the scope of the invention. The methods described may be applied to other catalysts and processes by those persons having ordinary skill based on the teachings, descriptions and examples included herein.

A fresh or untreated catalyst is a catalyst that is the result of direct synthesis of a catalytically active material by, for example, combination of an ammonium halide salt and an aluminum halide. It is a catalyst for which the basic synthesis steps have been done that produce a material having catalytic activity.

The specific examples used herein refer to alkylation processes using ionic liquid systems, which are amine-based cationic species mixed with aluminum chloride. In such systems, to obtain the appropriate acidity suitable for the alkylation chemistry, the ionic liquid catalyst is generally prepared to full acidity strength by mixing one molar part of the appropriate ammonium chloride with two molar parts of aluminum chloride. The catalyst exemplified for the alkylation process is an alkyl-pyridinium chloroaluminate, such as 1-butyl-pyridinium heptachloroaluminate.

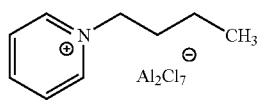

1-Butyl-pyridinium heptachloroaluminate

In general, a strongly acidic ionic liquid is necessary for alkylation, e.g. isoparaffin alkylation. In that case, aluminum chloride, which is a strong Lewis acid, in combination with a Broensted acid is a preferred catalyst component in the ionic liquid catalyst scheme.

Aluminum metal reacts with HCl to give hydrogen gas and $AlCl_3$. By introducing aluminum metal and HCl into fresh chloroaluminate ionic liquid catalysts aluminum chloride, which is the acidic component in the chloroaluminate ionic liquid, is produced in situ. As shown herein, the treated catalyst demonstrated better activity for the alkylation of ethylene with isopentane compared with freshly prepared catalyst.

An embodiment of a process according to the present invention utilizes in situ generated aluminum trichloride from the reaction between aluminum metal and hydrochloric acid to increase the activity of the freshly-made chloroaluminate ionic liquid catalyst. Using aluminum metal and HCl will produce $AlCl_3$ in situ which increases the acidity and the activity of the ionic liquid catalyst by increasing the concentration of $AlCl_3$ in the ionic liquid. Not to be bound by any theory, the in situ produced aluminum chloride perhaps aid in increasing the concentration of the active chloroaluminate species, such as $Al_2Cl_7^-$, $Al_3Cl_{10}^-$, in the ionic liquid and, thus, enhance the overall acidity and activity of the catalyst. In this way, the treated catalyst will be more active than the freshly prepared catalyst.

The metal used in a process in accordance with the present invention is not limited to aluminum. This process may be used for any Lewis acidic ionic liquid for which the reaction of a metal with a Bronsted acid will give the Lewis acidic component. For example, zinc metal and HCl can be used when the Lewis acidic component is $ZnCl_2$. Other metal whose metal halides may serve as Lewis acids include Fe, Cu, Ti, Sn, B, Ga, and In, among others. Aluminum metal will be the metal of choice when chloroaluminate ionic liquids are used in the catalytic process to avoid contamination of the ionic liquid catalyst with metal chlorides other than $AlCl_3$.

A process in accordance with the present invention is not limited to using HCl to produce the Lewis acid by reaction with the appropriate metal. Other Broensted acids may also be used but not limited to, HI, HBr, HF, $H_2SO4$, $H_3PO_4$. In the case of chloroaluminate ionic liquids, hydrohalides (HI, HCl, HBr, HF) will be the acids of choice. Among the hydrohalides hydrochloric acid is preferred to avoid introduction of conjugate bases other than halides and preferably other than chlorides.

As shown in the Examples which follow, fresh ionic liquid catalyst is treated with aluminum and hydrogen chloride. Adding aluminum and hydrogen chloride to fresh ionic liquid catalyst and stirring the resulting mixture (in autoclave) at temperatures ranging from 0-50° C. at autogenic pressures led to the production of a catalyst having greater activity than the fresh catalyst. The treated ionic liquid catalyst was removed from the remaining mixture (freshly made $AlCl_3$ and aluminum metal) by filtration.

The recovered activated ionic liquid catalyst was tested for activity by alkylating ethylene with isopentane and the catalyst showed better activity than the freshly-made catalyst before treatment. The selectivity of the treated catalyst was identical to the selectivity of the freshly-made catalyst.

In one embodiment of the present invention, a fresh ionic liquid catalyst is introduced continuously into a stirred tank reactor (CSTR), where aluminum metal powder is added by way of a screw-type feeder. The aluminum is kept under inert gas (nitrogen or other) to prevent oxidation. HCl gas is fed in at the desired rate to produce $AlCl_3$. The reaction product is withdrawn and mixed with a hydrocarbon solvent (e.g., hexane). The solvent may be a normal hydrocarbon ranging from $C_5$-$C_{15}$ and mixtures thereof, preferably $C_5$-$C_8$. This mixture is then separated in a gravity decanter, from which the denser ionic liquid phase is withdrawn. Unreacted aluminum is removed by filtration. The treated ionic liquid catalyst is recovered.

Reaction conditions will generally include temperatures of –20° C.-200° C., pressures of atmospheric—5000 psig, preferably atmospheric pressure—500 psig, and a contact time of 0.1 minute—24 hours, and preferably from ¼-2 hours in a normal hydrocarbon as a solvent.

A method in accordance with the present invention may be conducted as an integral part of the preparation of an acidic ionic liquid catalyst. It may be done in the same reaction system or in a separate reaction system.

The following Examples are illustrative of the present invention, but are not intended to limit the invention in any way beyond what is contained in the claims which follow.

EXAMPLES

Example 1

Preparation of Fresh 1-Butylpyridinium Chloroaluminate Ionic Liquid Catalyst A (Fresh IL A)

1-butyl-pyridinium chloroaluminate is a room temperature ionic liquid prepared by mixing neat 1-butyl-pyridinium chloride (a solid) with neat solid aluminum trichloride in an inert atmosphere. The syntheses of butylpyridinium chloride and the corresponding 1-butyl-pyridinium chloroaluminate are described below. In a 2-L Teflon-lined autoclave, 400 gm (5.05 mol.) anhydrous pyridine (99.9% pure purchased from Aldrich) were mixed with 650 gm (7 mol.) 1-chlorobutane (99.5% pure purchased from Aldrich). The neat mixture was sealed and let to stir at 125° C. under autogenic pressure over night. After cooling off the autoclave and venting it, the reaction mix was diluted and dissolved in chloroform and transferred to a three liter round bottom flask. Concentration of the reaction mixture at reduced pressure on a rotary evaporator (in a hot water bath) to remove excess chloride, unreacted pyridine and the chloroform solvent gave a tan solid product. Purification of the product was done by dissolving the obtained solids in hot acetone and precipitating the pure product through cooling and addition of diethyl ether. Filtering and drying under vacuum and heat on a rotary evaporator gave 750 gm (88% yields) of the desired product as an off-white shiny solid. $^1$H-NMR and $^{13}$C-NMR were consistent with the desired 1-butyl-pyridinium chloride and no impurities were observed.

1-Butylpyridinium chloroaluminate was prepared by slowly mixing dried 1-butylpyridinium chloride and anhydrous aluminum chloride ($AlCl_3$) according to the following procedure. The 1-butylpyridinium chloride (prepared as described above) was dried under vacuum at 80° C. for 48 hours to get rid of residual water (1-butylpyridinium chloride is hyroscopic and readily absorbs water from exposure to air). Five hundred grams (2.91 mol.) of the dried 1-butylpyridinium chloride were transferred to a 2-Liter beaker in a nitrogen atmosphere in a glove box. Then, 777.4 gm (5.83 mol.) of anhydrous powdered $AlCl_3$ (99.99% from Aldrich) were added in small portions (while stirring) to control the temperature of the highly exothermic reaction. Once all the $AlCl_3$ was added, the resulting amber-looking liquid was left to gently stir overnight in the glove box. The liquid was then filtered to remove any un-dissolved $AlCl_3$. The resulting acidic 1-butyl-pyridinium chloroaluminate was used as the catalyst for the alkylation of isopentane with ethylene.

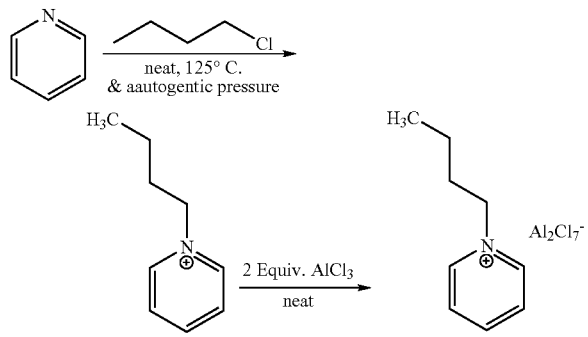

Example 2

Activation of IL A Using Al Metal and HCl

The activation was done in a batch reactor according to the following procedure. In a 300 cc autoclave, 75 gm of freshly made 1-butyl-pyridinium chloroaluminate ionic liquid, prepared as described in example 1, were mixed with 8 gm of aluminum powder in a an oxygen and water-free glove box under nitrogen. The autoclave was sealed and 5.5 gm of anhydrous HCl gas from a Lecture Bottle was added via an inlet. The mixture was then vigorously mixed with an overhead stirrer at ~>1200 rpm at room temperature and the autogenic pressure (230 psig at the start of the reaction) for only 15 minutes. The reaction temperature rose to ~30° C. and the pressure dropped to 203 psig. The autoclave (the reaction vessel) was vented off and let to cool back to room temperature. Then, the treated ionic liquid was filtered from the aluminum powder and the produced aluminum chloride. The filtered ionic liquid was somewhat milky in appearance due to the presence of excess $AlCl_3$ in the ionic liquid phase. The filtered catalyst was let to settle down and filtered again to give the treated (activated) catalyst as clear in appearance as the freshly-made catalyst. This catalyst was tested for activity by alkylating ethylene with isopentane according the procedure described in example 3.

Example 3

Determination of Activity of Treated IL A Using Batch Alkylation of isoPentane with Ethylene The alkylation of isopentane with ethylene was done according with the following procedure. A 300 cc autoclave was charged with 42 gm of ionic liquid catalyst, 100 gm of anhydrous isopentane, 12 gm of ethylene, and 0.3 gm of anhydrous HCl. The reaction was then stirred ~1200 rpm and heated to 50° C. at autogenic pressures. The starting pressure was usually 215-320 psi. The reaction was usually complete when the pressure dropped down to single digits. At the end of the reaction, the reactor was vented out and a gas sample was checked by GC for ethylene concentration. The liquid reaction mixture was allowed to settle into 2 phases. The organic phase was decanted and analyzed for product distribution by GC analysis. The following Table 1 draws a comparison between the freshly made and the treated catalysts.

TABLE 1

|  | Fresh Catalyst | Activated Catalyst |
|---|---|---|
| Reaction Time | 7 min. | 3 min. |
| Starting Pressure | 215 psi | 222 psi |
| Ending pressure | 7 | 4 |
| iC5 | 69.1 | 67.7 |
| C7s (total) | 19.1 | 20.3 |
| 2,3-DM-Pentane | 8.23 | 8.6 |
| 2,4-DM-Pentane | 10 | 9.7 |
| 2,3DM/2,4DM | 0.82 | 0.88 |

As shown in Table 1, the catalyst treated with HCl over aluminum metal reacted much quicker than the freshly-made untreated catalyst. While both catalysts led to identical products and selectivities, the treated catalyst appears to be more active based on the shorter time it required to complete the alkylation.

There are numerous variations on the present invention which are possible in light of the teachings and supporting examples described herein. It is therefore understood that within the scope of the following claims, the invention may be practiced otherwise than as specifically described or exemplified herein.

What is claimed is:

1. A process for producing acidic ionic liquid catalysts having enhanced activity comprising combining a fresh acidic ionic liquid catalyst, a metal and a Broensted acid for a time sufficient to increase the activity of the ionic liquid catalyst for alkylating a paraffin; wherein the Broensted acid is selected from the group consisting of HI, HBr, HF, $H_2SO_4$, $H_3PO_4$, and their mixtures.

2. The process according to claim 1, wherein the metal is selected from the group consisting of magnesium, aluminum, titanium, nickel, zinc, copper, iron, gallium, tin, indium, copper, zirconium, vanadium, niobium, chromium, molybdenum and their mixtures.

3. The process according to claim 1, wherein the metal is aluminum.

4. The process according to claim 1, wherein the conditions include contacting the ionic liquid catalyst with sufficient amounts of metal and excess acid at temperatures of −20° C.-200° C., pressures of atmospheric—5000 psig, and a contact time of 0.1 minute—24 hours in a normal hydrocarbon as a solvent.

5. The process according to claim 4, wherein the hydrocarbon solvent is selected from the group consisting of normal hydrocarbons ranging from $C_5$-$C_{15}$.

6. The process according to claim 1, wherein the ionic liquid catalyst comprises an imidazolium, pyridinium, phosphonium or tetralkylammonium derivative or their mixtures.

7. The process according to claim 1, wherein the ionic liquid catalyst is a chloroaluminate ionic liquid.

8. The process according to claim 6, wherein the ionic liquid catalyst is a chloroaluminate ionic liquid.

9. The process of claim 1, wherein the Bronstead acid is anhydrous.

* * * * *